United States Patent [19]

Beyer et al.

[11] Patent Number: 5,059,191
[45] Date of Patent: Oct. 22, 1991

[54] METHOD AND APPARATUS FOR THE IRRADIATION OF CAVITIES

[75] Inventors: Wolfgang Beyer, Munich; Armin Heinze, Ismaining; Ronald Sroka, Munich; Eberhard Unsöld, Oberschleissheim, all of Fed. Rep. of Germany

[73] Assignee: Gesellschaft für Strahlen-und Umweltforschung mbH (GSF), Neuherberg, Fed. Rep. of Germany

[21] Appl. No.: 494,662

[22] Filed: Mar. 16, 1990

[30] Foreign Application Priority Data

Mar. 25, 1989 [DE] Fed. Rep. of Germany ....... 3909843

[51] Int. Cl.⁵ .............................................. A61N 5/06
[52] U.S. Cl. .......................................... 606/2; 606/10; 128/395; 604/20
[58] Field of Search ...................... 606/2, 7, 13, 14–18, 606/10–12; 128/633, 634, 395, 397, 398; 604/20, 21; 362/350, 352, 320; 34/39

[56] References Cited

U.S. PATENT DOCUMENTS

| | | | |
|---|---|---|---|
| 3,939,340 | 2/1976 | Gozzano et al. | 362/320 |
| 4,470,407 | 10/1984 | Hussein | 128/6 |
| 4,512,762 | 4/1985 | Spears | 604/21 |
| 4,612,938 | 9/1986 | Dietrich et al. | 128/665 |
| 4,676,231 | 6/1987 | Hisazumi et al. | 128/6 |
| 4,693,556 | 9/1987 | McCangham, Jr. | 350/320 |
| 4,773,899 | 10/1988 | Spears | 604/20 |
| 4,799,479 | 1/1989 | Spears | 606/7 |
| 4,878,492 | 11/1989 | Sinofsky et al. | 128/303.1 |

Primary Examiner—Stephen C. Pellegrino
Assistant Examiner—Steven J. Shumaker
Attorney, Agent, or Firm—Spencer & Frank

[57] ABSTRACT

A method and an apparatus for the substantially uniform irradiation of the entire area of cavities from the inside. The apparatus comprises a light source and a layer comprising a material having a high-scatter capability, low transmission and low absorption, wherein said layer fits well to the interior surface of a cavity. The method comprises placing an area-covering layer along rhe cavity wall of the cavity to be irradiated with a material having a high diffusive reflection capability, low transmission, and low absorption capability to obtain a lined cavity; introducing a light source onto the interior of the lined cavity; and irradiating the lined cavity so that the light entering from the area-covering layer into the cavity wall is homogeneously distributed.

12 Claims, 2 Drawing Sheets

METHOD AND APPARATUS FOR THE IRRADIATION OF CAVITIES

CROSS REFERENCE TO RELATED APPLICATION

This application is related to application Ser. No. 39 09 843.5 filed Mar. 25, 1989 in the Patent Office of the Federal Republic of Germany, the entire disclosure of which is incorporated herein by reference.

BACKGROUND OF THE INVENTION

1. Field of the Invention

The present invention relates to a method and to an apparatus for the substantially uniform irradiation of the entire area of cavities from the inside. The method and apparatus are used to irradiate the walls of cavities such as, for example, internal hollow organs, with light. Uniform light distribution over the entire wall of the cavity is important in this connection.

2. Technology Review

Homogeneity is required, for example, for the integral photodynamic treatment of photo-sensitized tumors with laser light. A light dose that is too low locally does not completely kill off the tumor at that location and results in recurrences. Too high a light dose also damages healthy wall regions. Under certain circumstances, the tolerance range for the light dose is rather narrow.

Published application Ser. No. DE-OS 3,323,365 A1, which appears to correspond to U.S. Pat. No. 4,612,938, proposes a device in which a centrally ending glass fiber is inserted to transport light into spherical hollow organs, e.g. a urinary bladder. A liquid scattering medium filling the organ provides the homogeneity. A similar device is disclosed in Jocham et al, "Porphyrin Localization and Treatment of Tumors," 249-256 (1984).

Star et al, Photochemistry and Photobiology 46, No. 5, 619-624, (1987), irradiate cavities by means of a centrally placed radiator having an approximately cupola-shaped radiation characteristic.

Arnfield et al, "Lasers in Surgery and Medicine" 6, 150-156, (1986), describe a radiator having a cylindrical radiation characteristic that is inserted axially into cylindrical organs.

All of these devices require great accuracy in centering the central or axial radiator. Due to breathing and heartbeat movements, this accurate positioning is often almost impossible to accomplish, particularly in situations in which the irradiation device must be introduced into the cavity through a narrow catheter. Moreover, high demands are placed on the homogeneity of the radiation characteristic of these radiators which in most cases is imperfectly met.

Another drawback of these devices is that if the shape of the cavities deviates from the sphere or cylinder, these devices provide unsatisfactory results even if optimally adjusted.

It is an object of the invention to develop a method and an apparatus for the homogeneous irradiation of cavities in which irradiation homogeneity for different cavity shapes is ensured substantially independently of the position of the radiation source within the cavity.

SUMMARY OF THE INVENTION

A method is provided for substantially uniform irradiation of the entire area of a cavity from the inside comprising:

(a) placing an area-covering layer (2) comprising a material having a high diffusive reflection capability, low transmission and low absorption capability along the cavity wall (3) of the cavity to be irradiated to obtain a lined cavity;

(b) introducing a light source (1) into the interior of the lined cavity; and (c) irradiating the lined cavity so that the light entering from the area-covering layer into the cavity wall (3) is at least approximately homogeneously distributed.

An apparatus is provided for uniformly irradiating the entire area of a cavity from the inside comprising a light source (1), and a layer (2) comprising a material having a high back-scatter capability, low transmission and low absorption, wherein said layer fits well to the interior surface of a cavity.

BRIEF DESCRIPTION OF THE DRAWINGS

FIG. 1 shows a cavity of arbitrary shape in which a layer 2 lies closely against its interior wall 3. An example for the path of a light is shown that is emitted by a light source 1 disposed in the interior of the cavity and is reflected four times by the layer 2 before it enters the material surrounding the cavity through the interior wall 3 of the cavity.

FIG. 2 illustrates that the light impinging on the wall can be divided into different generations. Light of the "first generation" is assumed to come directly from the radiator. Light of the $n^{th}$ generation has already been reflected diffusely $n-1$ times by the wall. FIG. 2 is a schematic representation, employing an arbitrary example, of how the total light intensity impinging on the wall along any circumferential line is distributed over the various generations.

FIG. 3 shows the arrangement and parameters for the computer simulation to determine whether the non-homogenity resulting from non-central positioning of an isotropic spherical radiator in a hollow sphere is compensated by the invention. $I_{max}$ and $I_{min}$ represent the light intensity, and x and r represent the shift and radius, respectively.

FIG. 4 shows the relative light intensity (space irradiance) at the wall as a function of the shift x of the radiator toward the wall and of the reflectivity of the layer. For R=90%, the light intensity is almost independent of the position of the radiator over a large region.

DETAILED DESCRIPTION OF THE INVENTION

Figure 1:
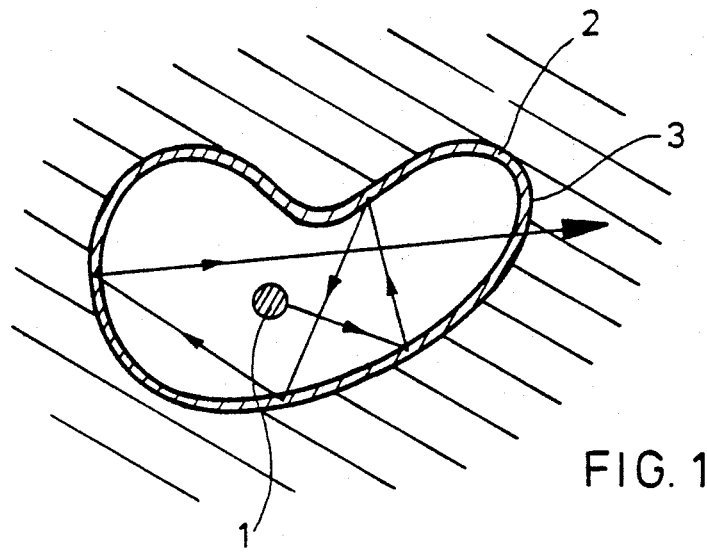
FIGS. 1 to 4 are schematic representations of the structure and effect of the homogenization of the radiation with the aid of multiple reflectors.

A method is provided for substantially uniform irradiation of the entire area of a cavity from the inside comprising:

(a) placing an area-covering layer (2) comprising a material having a high diffusive reflection capability, low transmission and low absorption capability along the cavity wall (3) of the cavity to be irradiated to obtain a lined cavity;

(b) introducing a light source (1) into the interior of the lined cavity; and (c) irradiating the lined cavity so that the light entering from the area-covering layer into the cavity wall (3) is at least approximately homogeneously distributed.

An apparatus is provided for uniformly irradiating the entire area of a cavity from the inside comprising a light source (1), and a layer (2) comprising a material having a high back-scatter capability, low transmission and low absorption, wherein said layer closely adheres to the interior surface of a cavity.

"Substantially uniform irradiation" and "uniformly irradiating" as used herein means irradiating as uniformly as possible. "At least approximately homogeneously distributed" means a light distribution measured in $Wm^{-2}$ which varies by not more than about ten percent at any point on the cavity wall.

Further embodiments of the method for uniformly irradiating the entire area of a cavity from the inside include that the layer (2) is sprayed onto the wall (3) of the cavity. Another embodiment of the method is that the layer (2) includes a light-hardenable component that is hardened by the irradiation so as to form a seal.

Further embodiments for the apparatus for uniformly irradiating the entire area of a cavity from the inside include that the layer (2) is elastic and is applied to the surface of an inflatable casing or a casing that can be filled with a liquid or a balloon. Further embodiments for the apparatus include that the layer (2) is an elastic casing that can be inflated or filled with a liquid. Further embodiments for the apparatus include that the layer (2) is an elastic casing that can be inflated or filled with a liquid, and said layer is applied to the surface of an inflatable casing or a casing that can be filled with a liquid or a balloon. Further embodiments for the apparatus include that the layer (2) is a self-supporting hollow body or a layer which is applied to a hollow or solid radiation transmitting carrier.

The apparatus for uniformly irradiating the entire area of a cavity from the inside may be used for photodynamic therapy or laser angioplastry, for example.

Advantages of the invention include noticeably more homogeneous distribution of the laser light to the various wall regions than without a back-scattering layer, and ensured homogeneity of the light distribution even if the light source is not positioned in the cavity in an accurately centered manner, that is, a higher positioning tolerance. Further advantages include reduced requirements for the shape of the radiation characteristic of the central light source, and sufficient homogeneity even if the cavity has an irregular geometry, e.g. no spherical or cylindrical shape.

It is of particular importance that the invention is suitable for a universal medical or technical irradiation concept, i.e. the irradiation devices can be similarly configured for different types of organs or cavity shapes. Under certain circumstances, it is possible to use, for example, a medical irradiation device for different organs.

DETAILED DESCRIPTION OF EMBODIMENTS

The invention will now be described in greater detail with reference to embodiments thereof that are illustrated in FIGS. 1 to 4. The figures are schematic representations of the structure and effect of the homogenization of the radiation with the aid of multiple reflections.

FIG. 1 shows a cavity of arbitrary shape in which a layer 2 lies closely against its interior wall 3. An example for the path of a light quantum is shown that is emitted by a light source 1 disposed in the interior of the cavity and is reflected four times by the layer 2 before it enters the material surrounding the cavity through the interior wall 3 of the cavity.

In a device for performing photodynamic therapy for photosensitized tumors, the light source is laser light of a suitable wavelength. This light travels into the hollow organ through flexible, light-conductive quartz fibers in a catheter or endoscope into the hollow organ. If it is desired to seal cavities with the aid of light hardenable and polymerizable plastic admixtures, e.g. epoxy resin, that are provided in the layer, then it is preferable to use ultraviolet light.

Layer 2 must be of such consistency that it back-scatters (diffusely reflects) the light from light source 1 with great probability and permits it to pass only with a low probability.

The light is emitted by a light source 1 disposed in the interior of the hollow organ but, on the average, will penetrate into the tissue only after several reflections and will be substantially homogeneously distributed over the entire cavity after a few reflections.

Figure 2:
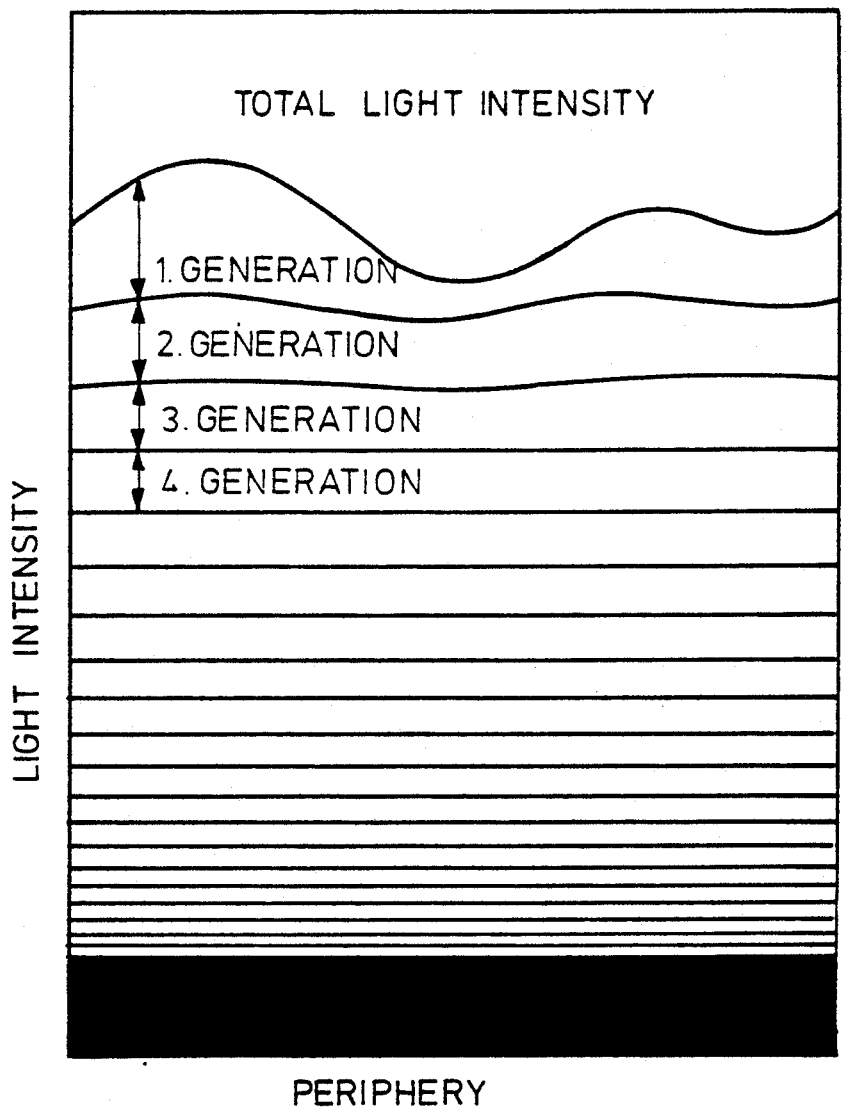

FIG. 2 illustrates the situation in greater detail. The light impinging on the wall can be divided into different generations. Light of the "first generation" is assumed to come directly from the radiator. Light of the $n^{th}$ generation has already been reflected diffusely $n-1$ times by the wall. FIG. 2 is a schematic representation, employing an arbitrary example, of how the total light intensity impinging on the wall along any circumferential line is distributed over the various generations. The light of the first generation may be distributed very nonhomogeneously. Due to the diffuse reflections, the light of the higher generation has so-to-speak "forgotten" its origin and is therefore distributed with increasing homogeneity.

Since, for example, about 10% of the light of each generation is intended to penetrate into the wall and thus—aside from the unavoidable absorption losses in the layer itself—leaves the cavity, the intensity of the light decreases slightly from generation to generation. The sum of all higher generations nevertheless clearly dominates (for example, by a factor of 10) the share of the first generation so that the total light distribution is now at least approximately homogeneous.

The homogeneity of the light is caused by a scattering medium which, in contrast to prior attempts, is not concentrated or not only concentrated in the center of the cavity (spherical radiators) and also does not uniformly fill the cavity. By contrast, the scattering medium is present in the form of a thin layer in the vicinity of the wall.

The principle is different from the Ulbricht sphere because for an Ulbricht sphere it is desired to have $R=100\%$ and the light is recorded at only one small wall location (detector). In contrast, for the present invention a value slightly less than $R=100\%$ is desired and the part of the light which penetrates into the wall is utilized. Moreover, the present invention also applies to non-spherical cavities.

The optical characteristics of the layer must meet the following requirements. Its back scattering capability (diffuse reflectivity) (R) must be clearly greater than its transmission T so as to realize high homogeneity. Additionally, its transmission (T) should be clearly higher than its absorption (A) in order to attain high efficiency (see below). R, T and A refer to the case of a one-time interaction between the light and the layer. The reflection must be diffuse in order to prevent undesirable focusing effects on the oppositely disposed wall region. It is difficult to attain values for absorption below 1% in the optical domain so that a suitable layer should have R=90%, T=9% and A=1%.

Such layers may be produced from a white pigment (e.g. $BaSO_4$ or $TiO_2$) embedded in a suitable carrier, such as a transparent plastic. By selecting the pigment concentration and the layer thickness, the desired values of R and T can be easily realized with $A \leq 1\%$. The layer may be applied directly onto the wall, e.g. sprayed on; it may be realized in the form of a balloon which, when inflated, adapts itself to the shape of the cavity; or it may be introduced into the cavity as a rigid structure, either as a self-supporting hollow structure or applied to a hollow or solid light-transmitting carrier.

One example for a layer 2 comprising a material having the desired transmission, reflection and absorption characteristics is a mixture of RTV silicone rubber VP 7660 and color paste FL (50% $TiO_2$) produced by Wacker-Chemie, Burghausen, Federal Republic of Germany, in a ratio of about 9 to 1 (RTV silicone rubber VB 7660 to color paste FL (50% $TiO_2$)) for a layer thickness of 0.5 mm.

The efficacy is assumed to be measured by the ratio of the light energy penetrating into the tissue to the total energy of the radiator in the hollow organ. It is $T/(T+A)$ and results from the ratio of the loss mechanism for light in the cavity viscus, namely the favorable loss mechanism T (light penetrates into the tissue) to the sum of all loss mechanisms, i.e. $T+A$. Therefore, for example, for R=90%, T=9%, A=1%, the efficacy is 90% and not 9% as was initially assumed.

Figure 3:
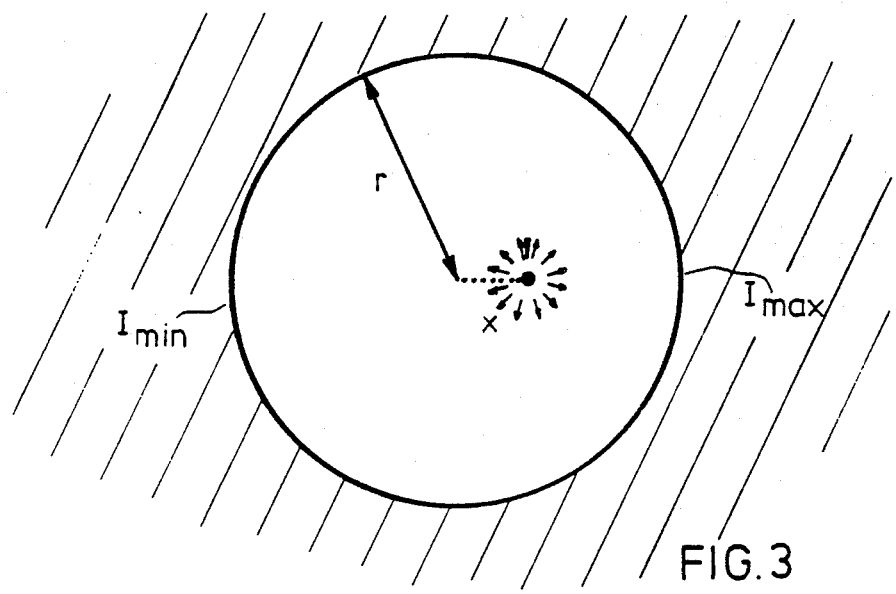

Using computer simulation we examined whether the nonhomogeneity resulting from non-central positioning of an isotropic spherical radiator in a hollow sphere is compensated by the invention. FIG. 3 shows this arrangement with the parameters relevant for the simulation.

Figure 4:
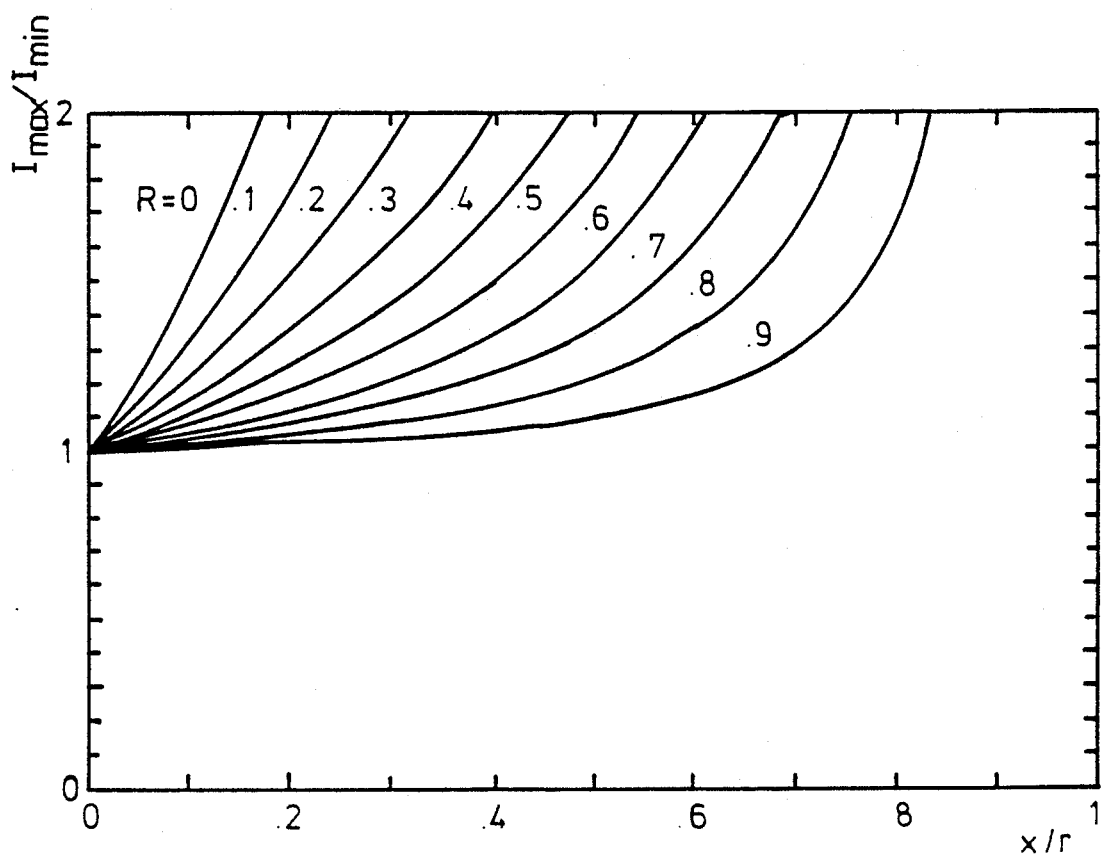

FIG. 4 shows the relative light intensity (space irradiance) at the wall as a function of the shift x of the radiator toward the wall and of the reflectivity of the layer. For R=90%, the light intensity is almost independent of the position of the radiator over a large region. According to corresponding computer simulations for the irradiation in cylinders, such as, for example, tubular organ structures, the light is even more effectively homogenized.

If the second generation is already almost homogeneous, as is the case, for example, for spherical organs, the intensity fluctuations are reduced by a factor of $1/(1-R)$ as can be demonstrated by way of an estimation employing geometrical series, that is for R=90%, for example, by a factor of 10.

In addition to its use in photodynamic cancer therapy, the device according to the invention is also suitable for the irradiation of plaque and stenosis areas in photodynamic angioplasty.

A layer adapted in its thickness to the wavelength of microwaves and with adapted dielectric constant produces a homogeneous distribution of the radiation in large-volume microwave instruments.

While the invention has been described in connection with specific embodiments thereof, it will be understood that it is capable of further modification and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for substantially uniform irradiation of the entire area of a cavity from the inside comprising:
   (a) placing an area-covering layer comprising a material having a high diffusive reflection capability, low transmission and low absorption capability along the cavity wall of the cavity to be irradiated to obtain a lined cavity;
   (b) introducing a light source into the interior of the lined cavity; and
   (c) irradiating the lined cavity so that the light entering from the area-covering layer into the cavity wall is at least approximately homogeneously distributed.

2. The method as defined in claim 1, wherein the placing step is accomplished by spraying layer onto the wall of the cavity.

3. The method as defined in claim 2, wherein the layer includes a light-hardenable component.

4. The method as defined in claim 3, further comprising hardening said layer including a light-hardening component by irradiation so as to form a seal.

5. The method as defined in claim 1, wherein the layer includes a light-hardenable component.

6. The method as defined in claim 5, further comprising hardening said layer including a light-hardening component by irradiation so as to form a seal.

7. An irradiation kit for uniformly irradiating the interior of a cavity comprising a layer of a material having a high back-scatter capability, low transmission and low absorption, said layer being adapted to conform to the shape of the interior surface of the cavity to form a lined cavity, and a light source adapted to be placed within the lined cavity.

8. The irradiation kit as defined in claim 7, wherein the layer is elastic and is applied to the surface of an inflatable casing.

9. The irradiation kit as defined in claim 7, wherein the layer is an elastic casing that can be inflated.

10. The irradiation kit as defined in claim 7, wherein the layer is an elastic casing that can be inflated, and said layer is applied to the surface of an inflatable casing.

11. The irradiation kit as defined in claim 7, wherein the layer is a self-supporting hollow body.

12. The irradiation kit as defined in claim 11, wherein the layer is applied to a radiation transmitting carrier.

* * * * *